(12) United States Patent
Chakraborty et al.

(10) Patent No.: US 12,234,201 B2
(45) Date of Patent: Feb. 25, 2025

(54) MAKING ETHYLENEDIAMINETETRAACETIC ACID

(71) Applicants: Dow Global Technologies LLC, Midland, MI (US); Dow Silicones Corporation, Midland, MI (US)

(72) Inventors: Deboleena Chakraborty, Midland, MI (US); Edward D. Daugs, Midland, MI (US); Kenneth E. Stockman, Midland, MI (US); Ronald Peterson, Midland, MI (US)

(73) Assignees: Dow Global Technologies LLC, Midland, MI (US); Dow Silicones Corporation, Midland, MI (US)

( * ) Notice: Subject to any disclaimer, the term of this patent is extended or adjusted under 35 U.S.C. 154(b) by 578 days.

(21) Appl. No.: 17/603,846

(22) PCT Filed: Jun. 3, 2020

(86) PCT No.: PCT/US2020/035805
§ 371 (c)(1),
(2) Date: Oct. 14, 2021

(87) PCT Pub. No.: WO2020/251812
PCT Pub. Date: Dec. 17, 2020

(65) Prior Publication Data
US 2022/0234993 A1    Jul. 28, 2022

Related U.S. Application Data

(60) Provisional application No. 62/861,147, filed on Jun. 13, 2019.

(51) Int. Cl.
*C07C 227/02*    (2006.01)
*C07C 255/25*    (2006.01)

(52) U.S. Cl.
CPC .......... *C07C 227/02* (2013.01); *C07C 255/25* (2013.01)

(58) Field of Classification Search
CPC .... C07C 227/02; C07C 255/25; C07C 253/30
See application file for complete search history.

(56) References Cited

U.S. PATENT DOCUMENTS

| | | | | |
|---|---|---|---|---|
| 2001/0007042 A1* | 7/2001 | Van Doorn | ........... | C07C 227/00 562/565 |
| 2011/0288332 A1* | 11/2011 | Moore, Jr. | ........... | C07C 227/26 562/554 |

FOREIGN PATENT DOCUMENTS

| | | | | |
|---|---|---|---|---|
| CN | 1718569 A | * | 1/2006 | |
| CN | 106045867 A | * | 10/2016 | |
| DE | 638071 C | | 11/1936 | |
| EP | 0085277 B1 | * | 9/1985 | |
| WO | 2013/030287 A1 | | 3/2013 | |

OTHER PUBLICATIONS

PubChem CID 101815794, National Center for Biotechnology Information. "PubChem Compound Summary for CID 101815794, 2-[2-[Carboxymethyl(cyanomethyl)amino]ethyl-(cyanomethyl)amino]acetic acid" PubChem, https://pubchem.ncbi.nlm.nih.gov/compound/101815794. Accessed Jul. 11, 2024, create date Dec. 18, 2015. (Year: 2015).*
Masuzawa et al. "Syntheses and Reactions of Nitrogen- and Sulfur-Analogs of 2-Piperazinone" Bull. Soc. Chem. Japan 1968, 41, 702 (Year: 1968).*

(Continued)

*Primary Examiner* — Amanda L. Aguirre
(74) *Attorney, Agent, or Firm* — James T. Hoppe

(57) ABSTRACT

Provided is a method of making ethylenediaminetetraacetic acid (EDTA) comprising the steps:

(a) providing a reaction mixture (a) comprising ethylenediamine (EDA) and glycolonitrile (GN), wherein reaction mixture (a) comprises 0% to 0.1% by weight, based on the weight of reaction mixture (a), of any base having pKa of the conjugate acid (PKaH) of 13 or higher;

(b) causing or allowing reaction mixture (a) to react to form a dinitrile (DN) compound;

(c) bringing the DN into contact with aqueous solution of a base having pKaH of 11 or higher, and causing or allowing the resulting mixture to react to form a diacid compound (DA);

(d) causing or allowing the DA to react, either sequentially or simultaneously, with additional GN to form products (Pd);

(e) causing or allowing products (Pd) to react with a base having pKaH of 11 or higher, to form EDTA.

Also provided is a composition comprising a diacid/dinitrile compound (DADN) wherein each —R has the structure:

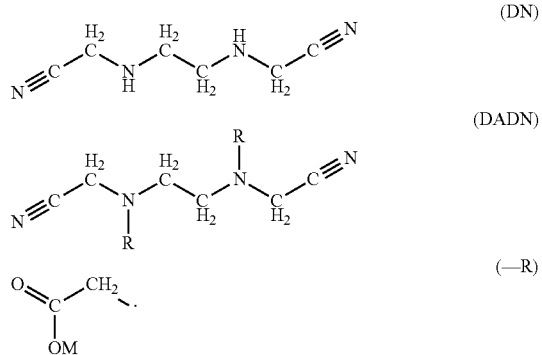

6 Claims, No Drawings

(56) References Cited

OTHER PUBLICATIONS

Ji et al. "Method of preparing ethylenediamine tetracetonitrile and ethylenediamine tetraacetic acid using hydroxy acetonitrile as raw material" CN-1718569-A, English machine translation, retrieved from https://patents.google.com on Nov. 16, 2024. (Year: 2024).*
PCT/US2020/035805, International Search Report and Written Opinion with a mailing date of Aug. 25, 2020.
https://pubchem.ncbi.nlm.nih.gov/compound/101815794, 2020, pp. 1-7.
Roscoe Smith et al., J. of Organic Chemistry, 1949, pp. 355-361, vol. 14.

* cited by examiner

MAKING ETHYLENEDIAMINETETRAACETIC ACID

Ethylenediamine tetraacetic acid (EDTA) is a chemical compound that has many important industrial uses, for example as a ligand and/or chelating agent for metals. Prior to the present invention, a process commonly used to produce EDTA involves addition of glycolonitrile (GN) to ethylenediamine (EDA) in the presence of aqueous sodium hydroxide. A problem with this process is that it produces, in addition to EDTA, the undesirable byproduct nitrilotriacetic acid (NTA). NTA is undesirable because it is suspected to be a carcinogen. It is desired to provide an improved method of making EDTA that reduces the production of NTA. Independently, another goal is to provide a method of making EDTA that minimizes the production of color bodies.

CN106045867A describes a process of making ethylenediamine-N—N'-diacetate (DA). In the first step, EDA is added to GN to produce the dinitrile derivative of EDA (DN), and in a subsequent step, DN is converted to DA. While CN106045867A teaches a method of making DA, it is desired to provide a method of making EDTA.

The following is a statement of the invention.

A first aspect of the present invention is a method of making ethylenediaminetetraacetic acid (EDTA) comprising the steps:

(a) providing a reaction mixture (a) comprising ethylenediamine (EDA) and glycolonitrile (GN), wherein reaction mixture (a) comprises 0% to 0.1% by weight, based on the weight of reaction mixture (a), of any base having pKa of the conjugate acid (pKaH) of 13 or higher;

(b) causing or allowing reaction mixture (a) to react to form a dinitrile compound having structure DN:

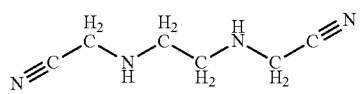
(DN)

(c) bringing the DN into contact with aqueous solution of a base having pKaH of 11 or higher, and causing or allowing the resulting mixture to react to form a diacid compound having structure DA:

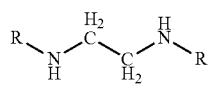
(DA)

wherein each —R has the following structure:

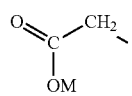

wherein each M is independently hydrogen or an alkali metal or a mixture thereof;

(d) causing or allowing the DA to react, either sequentially or simultaneously, with additional GN to form products (Pd);

(e) causing or allowing products (Pd) to react with a base having pKaH of 11 or higher, to form EDTA.

A second aspect of the present invention is a composition comprising a compound with the structure DADN:

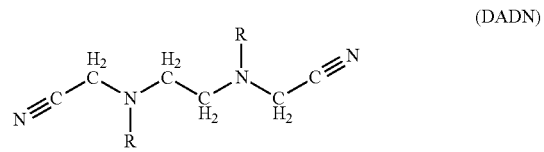
(DADN)

wherein each —R has the structure:

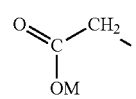

wherein each M is independently hydrogen or an alkali metal or a mixture thereof.

The following is a detailed description of the invention. The following definitions are used herein, unless the context specifically states otherwise.

Ratios presented herein are characterized as follows. For example, if a ratio is said to be 3:1 or greater, that ratio may be 3:1 or 5:1 or 100:1 but may not be 2:1. This characterization may be stated in general terms as follows. When a ratio is said herein to be X:1 or greater, it is meant that the ratio is Y:1, where Y is greater than or equal to X. For another example, if a ratio is said to be 15:1 or less, that ratio may be 15:1 or 10:1 or 0.1:1 but may not be 20:1. In general terms, when a ratio is said herein to be W:1 or less, it is meant that the ratio is Z:1, where Z is less than or equal to W.

The following abbreviations are used herein to denote the following chemical structures. In all the structures shown, —R has the same meaning.

| Abbreviation | Description | Structure |
|---|---|---|
| EDA | Ethylenediamine | $H_2N-CH_2-CH_2-NH_2$ |
| GN | Glycolonitrile | $N{\equiv}C-CH_2-OH$ |
| DN | dinitrile | (structure as shown) |
| -R | acetic acid group | $O{=}C(CH_2-)-OM$ | where M is hydrogen or an alkali metal atom or a mixture thereof
(The dangling bond on the right side denotes the connection this "group" makes to another molecule)

| Abbreviation | Description | Structure |
|---|---|---|
| DA | diacid | 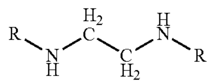 |
| DADN | diacid/dinitrile | 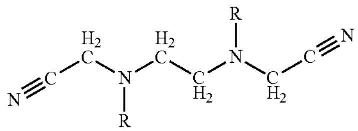 |
| EDTA | ethenediamine tetraacetic acid | 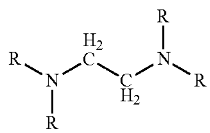 |
| NTA | nitrilotriacetic acid | 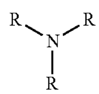 |
| SEDDA | symmetrical ethylenediamine-N—N'-diacetic acid | 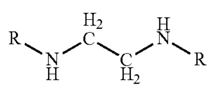 |
| UEDDA | unsymmetrical ethylenediamine-N—N'-diacetic acid | 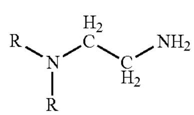 |
| ED3A | ethylenediamine-triacetic acid | 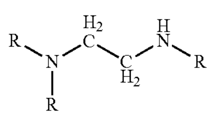 |

Note: for each of DA, DN, and DADN, more than one isomer is possible. For each of these three compounds, the compound in question may be any pure isomer or may be any mixture of one or more isomer. For example, UEDDA and SEDDA are isomers of DA.

As used herein, the term "very strong base" is defined as follows. A base is a compound that is capable of attaching to a hydrogen atom to form the conjugate acid of the base. The dissociation reaction of the conjugate acid is shown as follows in reaction (I):

$$HB \rightleftharpoons H^+ + B^- \qquad (I)$$ 

Where B is the base compound, H is the hydrogen atom, and HB is the conjugate acid of the base compound. In some cases, for example if B⁻ is OH⁻, the moiety shown in (I) as B⁻ is indeed negatively charged as shown in reaction (I). In other cases, for example if the moiety shown as B⁻ is pyridine, then the moiety shown as HB is, in reality, positively charged, and the moiety shown as B⁻ is, in reality, neutral. The negative logarithm of the equilibrium constant of reaction (I) is the pKa of the conjugate acid HB, and this quantity herein is denoted pKaH, to denote that this quantity is the pKa of the conjugate acid of the base compound of interest. A base compound is considered herein to be a "very strong" base if the pKaH of that base compound is 13 or higher. A base compound is considered herein to be a "moderately strong" base if the pKaH of that base compound is 12 or higher and if the pKaH of that base compound is less than 13. A base compound is considered herein to be a "mildly strong" base if the pKaH of that base compound is 11 or higher and if the pKaH of that base compound is less than 12.

For example, hydroxide ion (Off) has pKaH of 14 and is a very strong base. For another example, EDA has pKaH of approximately 9.9 and does not fall within any of the following categories: mildly strong base, moderately strong base, or very strong base.

When it is stated herein that a compound is added to a vessel at a "steady rate," the following is meant: we label the period of time over which the compound is added as "$T_{total}$"; we consider any interval of time (labeled T10) that is 10% of the duration of $T_{total}$ and that falls completely within the period of time $T_{total}$; the rate of addition of the compound is "steady" if, regardless of the choice of T10, the amount of compound added during T10 is from 5% to 15% of the total of all of the compound added during the period $T_{total}$.

The process of the present invention produces EDTA. The EDTA that is formed may be in acid form, in salt form, or a mixture thereof. That is, in the structure shown above, each M may independently be hydrogen or may be an alkali metal. All four R groups on an EDTA molecule may be hydrogen as M, or all four R groups on an EDTA molecule may be alkali metal as M, or an EDTA molecule may have one or more R groups in which M is hydrogen and one or more R groups in which M is an alkali metal. Further, it is possible that a mixture of EDTA molecules may be present that have differing numbers of R groups in which M is hydrogen.

The process of the present invention involves a step in which a reaction mixture (a) is provided. Reaction mixture (a) contains, possibly among other compounds, ethylenediamine (EDA) and glycolonitrile (GN). Reaction mixture (a) contains little or no very strong base. That is, either no very strong base is present in reaction mixture (a), or, if any very strong base is present, the total amount of very strong base is 0.1% or less, by weight based on the weight of the reaction mixture (a). Preferably, the total amount of very strong base is 0 to 0.03%; more preferably 0 to 0.01%; more preferably zero.

Preferably, during step (a) the amount of moderately strong base in reaction mixture (a), by weight based on the weight of reaction mixture (a), is 0 to 0.1%; more preferably 0 to 0.03%; more preferably 0 to 0.01%; more preferably zero. Preferably, the amount of mildly strong base in reaction mixture (a), by weight based on the weight of reaction mixture (a), is 0 to 0.1%; more preferably 0 to 0.03%; more preferably 0 to 0.01%; more preferably zero.

Preferably, little or no hydroxide ion is present in reaction mixture (a). That is, preferably the amount of hydroxide ion in reaction mixture (a) is, by weight based on the weight of reaction mixture (a), 0 to 0.1%; more preferably 0 to 0.03%; more preferably 0 to 0.01%.

In reaction mixture (a), the mole ratio of GN to EDA is preferably 0.1:1 or higher; more preferably 0.3:1 or higher; more preferably 1:1 or higher; more preferably 1.5:1 or higher. In reaction mixture (a), the mole ratio of GN to EDA is preferably 3:1 or lower; more preferably 2:1 or lower.

Reaction mixture (a) may be at any temperature. Preferably, reaction mixture (a) is at temperature of −10° C., 0° C., or higher. Preferably, reaction mixture (a) is at temperature of 100° C. or lower; more preferably 50° C. or lower; more preferably 25° C. or lower; more preferably 10° C. or lower.

Reaction mixture (a) may be formed by any method. For example, GN (neat or in an aqueous solution) may be placed in a vessel, and then EDA (neat or in an aqueous solution) may be added gradually at a steady rate to the vessel. For another example, GN (neat or in an aqueous solution) and EDA (neat or in an aqueous solution) may be simultaneously added to a vessel in a semi-continuous process. In other embodiments ("GN-add" embodiments), EDA (neat or in aqueous solution) is placed in a vessel, and then GN (neat or in aqueous solution) is gradually added (preferably at a steady rate) to the vessel; in these GN-add embodiments, preferably, prior to the beginning of the addition of the GN, the amount of GN in the vessel is, by weight of GN based on the weight of EDA in the vessel, 0 to 0.1%; more preferably 0 to 0.01%; more preferably zero.

Preferably, GN and EDA are brought together in a manner that controls the temperature of the resulting reaction mixture (a). Whether GN is added to EDA or EDA is added to GN or whether the two are simultaneously added to a vessel, is preferable that the conditions are chosen so that the temperature ("TA") of reaction mixture (a) does not exceed a value TA-Max. The conditions include, for example, one or more of the following: rate of addition, mechanical agitation, and/or externally applied cooling via heat exchange. Preferably, TA-Max is 40° C. or lower; more preferably 30° C. or lower; more preferable 20° C. or lower; more preferably 15° C. or lower; more preferably 10° C. or lower. Preferably, TA is 0° C. or higher.

Preferably, prior to bringing EDA into contact with GN to form reaction mixture (a), the EDA is either neat or is in aqueous solution. Preferably, the EDA is in an aqueous solution, and preferably the concentration of EDA, by weight based on the weight of the aqueous solution, is 30% to 100%; more preferably 50% to 100%; more preferably 60% to 100%. It is meant herein that an aqueous solution having concentration of EDA of 100% is neat EDA and does not contain water.

Preferably, prior to bringing EDA into contact with GN to form reaction mixture (a), the GN is in the form of an aqueous solution. Preferably, the concentration of GN in that solution is 10% or higher; more preferably 20% or higher; more preferably 30% or higher. Preferably, the concentration of GN in that solution is 70% or lower; more preferably 60% or lower; more preferably 50% or lower.

Preferably, the total amount of all compounds in reaction mixture (a) other than EDA, GN, and water is, by weight based on the weight of reaction mixture (a), 0 to 3%; more preferably 0 to 1%; more preferably 0 to 0.3%; more preferably 0 to 0.1%; more preferably 0 to 0.03%.

Reaction mixture (a) may be held under an inert atmosphere or may be exposed to air.

In the practice of the present invention, in step (b), a chemical reaction occurs in reaction mixture (a) in which EDA reacts with GN to form a mixture of products (Pb) that contains the dinitrile compound DN defined above. Then, in step (c), DN is brought into contact with an aqueous solution that contains a base, which may be either a mildly strong base (i.e., pKaH of 11 or higher and lower than 12), or a moderately strong base (i.e., pKaH of 12 or higher and less than 13), or a strong base (i.e., pKaH of 13 or higher). This base is labeled herein as base (Bc). Preferably, base (Bc) is a moderately strong base or a very strong base; more preferably, base (Bc) is a very strong base.

Preferably, base (Bc) is hydroxide ion. Preferably, the hydroxide ion is introduced as an aqueous solution of an alkali metal hydroxide, preferably sodium hydroxide. Potassium hydroxide can also be used.

Compound DN may be brought into contact with the aqueous solution of base (Bc) by any method. Preferably, the mixture of products (Pb) formed in step (b) is used without further purification or separation. Optionally, water may be added to products (Pb) prior to step (c). In some embodiments, the aqueous solution of base (Bc) is gradually added to a vessel that contains DN (either neat or in a solution or in the products (Pb)). In preferred embodiments, DN (either neat or in a solution or in the products (Pb)) is gradually added to a vessel that contains the aqueous solution of base (Bc).

Regardless of the form of DN that is brought into contact with aqueous solution of base (Bc), in embodiments in which DN is added to aqueous solution of base (Bc), it is preferred that the DN is added gradually (preferably at a steady rate) under conditions that maintain the temperature of the mixture ("TC") that contains DN and base (Bc) below a value of TC-Max. Conditions include, for example, one or more of rate of addition of DN, mechanical agitation, and/or externally applied heating and/or cooling. Preferably TC-Max is 90° C. or lower; more preferably 70° C. or lower; more preferably 60° C. or lower; more preferably 45° C. or lower. Preferably, TC is 0° C. or higher.

In the aqueous solution of base (Bc), prior to contact with DN, preferably the concentration of base (Bc), by weight based on the weight of the aqueous solution, is 10% or more; more preferably 20% or more; more preferably 30% more. In the aqueous solution of base (Bc), preferably the concentration of base (Bc), by weight based on the weight of the aqueous solution, is 75% or less; more preferably 70% or less; more preferably 65% or less; more preferably 55% or less; more preferably 50% or less.

In step (c), preferably the mole ratio of base (Bc) to DN is 2:1 or higher; more preferably 3:1 or higher; more preferably 4:1 or higher. In step (c), preferably the mole ratio of base (Bc) to DN is 6:1 or less; more preferably 5:1 or less.

Preferably, the chemical reaction in step (c) is conducted at temperature of 0° C. or higher; more preferably 10° C. or higher. Preferably, the chemical reaction in step (c) is conducted at temperature of 100° C. or lower; more preferably 90° C. or lower; more preferably 65° C. or lower; more preferably 55° C. or lower; more preferably 45° C. or lower.

In step (c), after the DN and the base (Bc) have been brought together, the resulting mixture is caused or allowed to undergo a chemical reaction to form products (Pc) that contain the diacid compound DA defined above. It is contemplated that this reaction will also produce ammonia, which may be released to the atmosphere as ammonia gas or may be dissolved in water as ammonium hydroxide or may be a mixture thereof. Preferably, if ammonia is dissolved in water, the ammonia is preferably removed. Removal methods include, for example, air sparging, nitrogen sparging, and vacuum distillation. When sparging is performed, it may be performed during or after the chemical reaction. Preferably the amount of ammonia dissolved in the water is, by weight based on the weight of ammonia produced in the chemical reaction that formed products (Pc), 10% or less; more preferably 5% or less; more preferably 2% or less; more preferably 1% or less.

In the compound DA that is formed, the moiety M that is attached to the carboxyl groups may be hydrogen, an alkali metal, or a mixture thereof. Preferred alkali metal is sodium or potassium. Preferably, the mole percent of the carboxyl groups on the DA molecules for which M is an alkali metal is 50% or more; more preferably 75% or more; more preferably 90% or more.

Subsequent to step (c), step (d) is performed. In step (d), the compound DA is brought into contact with GN. Some or all of the GN used in step (d) is in addition to the GN that was used in steps (a) and (b). Step (d) may be performed by any method. In a preferred embodiment, the products (Pc) produced by step (c) are brought into contact with GN. Prior to contact with the products (Pc), the GN is preferably in the form of an aqueous solution. Preferably, the concentration of GN in the aqueous solution is, by weight based on the weight of the aqueous solution, is 25% or higher; more preferably 35% or higher. Preferably, the concentration of GN in the aqueous solution is, by weight based on the weight of the aqueous solution, is 55% or lower; more preferably 45% or lower.

In some embodiments, the GN (possibly in the form of an aqueous solution) is preloaded in a vessel, and the products (Pc) are added to that vessel. In some embodiments, the GN (possibly in the form of an aqueous solution) the products (Pc) are both gradually added to a vessel. In some embodiments, two continuous streams, one containing GN and the other containing products (Pc), are brought into contact prior to adding the mixed streams to a vessel. In preferred embodiments, the products (Pc) are resident in a vessel, and the GN is gradually added to that vessel, preferably at a steady rate, as defined above. When GN is gradually added, the total time for the addition of GN is preferably 30 minutes or more; more preferably 1 hour or more. When GN is gradually added, preferably the conditions are chosen so the temperature in the vessel ("TD") remains equal to or greater than TD-Min and remains equal to or less than TD-Max. The conditions include, for example, one or more of rate of addition, mechanical agitation, and/or externally applied heating and/or cooling via heat exchange. Preferably, the TDd-Min is 40° C. or higher; more preferably 60° C. or higher; more preferably 80° C. or higher; more preferably 90° C. or higher. Preferably, TD-Max is 120° C. or lower; more preferably 100° C. or lower.

In step (d), it is useful to assess the mole ratio of GN to DA. The GN used in assessing the mole ratio includes the total of all GN added during any or all of the steps (a), (b), (c), and (d). Preferably that mole ratio is 3.5:1 or higher; more preferably 4:1 or higher. Preferably that mole ratio is 5:1 or lower; more preferably 4.5:1 or lower; more preferably 4.2 or lower; more preferably 4.1 or lower.

In the performance of step (d), the DA and the GN are caused or allowed to react to produce products (Pd). It is contemplated that the products (Pd) contain, possibly among other compounds, the diacid/dinitrile compound DADN, as defined above.

Subsequent to step (d), step (e) is performed. In step (e), products (Pd) are in contact with an aqueous solution of a base having pKaH or 11 or higher. The products (Pd) are caused or allowed to react with the base having pKaH of 11 or higher; it is contemplated that this reaction will produce, possibly among other compounds, EDTA. The EDTA may be in acid form, in salt form, or a mixture thereof. It is contemplated that this reaction will also produce ammonia, which may be released to the atmosphere as ammonia gas or may be dissolved in water as ammonium hydroxide or may be a mixture thereof. Ammonia is that is dissolved in water is preferably removed, as described above regarding step (c).

In some embodiments, a mixture is formed that contains DA, GN, and an aqueous solution of base having pKaH of 11 or higher. In such embodiments, it is contemplated that DA and GN will react to form DADN, and the DADN will react in turn with the base having pKaH of 11 or higher to form EDTA. Thus, in such embodiments, step (d) will occur and then step (e) will occur, all within the same container.

In some preferred embodiments, the DA used in step (d) is in the form of the products (Pc) from step (c). In such embodiments, it is anticipated that the mixture that is formed by bringing GN and products (Pc) together will contain some of base (Bc). It is contemplated that the base (Bc) will react with DADN to produce EDTA. In these preferred embodiments, it is noted that, while the sequence of chemical reactions that take place include step (d) followed by step (e), all the necessary reactants for both steps (d) and (e) are present in the mixture that is formed by bringing GN and products (Pc) together. Thus, in these preferred embodiments, step (e) occurs without the necessity of adding any additional reactants.

In the compound EDTA that is formed, the moiety M that is attached to the carboxyl groups may be hydrogen, an alkali metal, or a mixture thereof. Preferred is one or more alkali metal, more preferably sodium, potassium, or a mixture thereof. Preferably, the mole percent of the carboxyl groups on the EDTA molecules for which M is an alkali metal is 50% or more; more preferably 75% or more; more preferably 90% or more.

After step (e) has concluded, it is useful to characterize the composition of the resulting mixture, herein labeled product mixture (Pe). The amount of each compound is characterized as a weight percent, based on the total solid weight of product mixture (Pe). The total solid weight of product mixture (Pe) includes the weight of water and excludes the weight of ammonia. Preferably, product mixture (Pe) contains EDTA and ED3A. Preferably, the amount of EDTA is 10% or more; more preferably 15% or more; more preferably 20% or more. In some embodiments, the amount of EDTA is 50% or less.

In product mixture (Pe), preferably the amount of ED3A is 10% or less; more preferably 5% or less; more preferably 2% or less; more preferably 1% or less. ED3A is not a desired product of the process. Hover, in some embodiments, some ED3A may be present in product mixture (Pe), in amounts, for example, of 0.1% or more; or 0.2% or more.

In product mixture (Pe), preferably the amount of NTA is 3% or less; more preferably 2.5% or less. In product mixture (Pe), in some embodiments, some NTA is present. Most preferably, the amount of NTA is zero.

It is also useful to characterize product mixture (Pe) by the weight ratio of EDTA to NTA. It is desired that this ratio be as high as possible. Preferably, the weight ratio of EDTA to NTA is 7:1 or higher; more preferably 8:1 or higher; more preferably 9:1 or higher.

While the present invention is not limited to any specific mechanism, the following reasoning is contemplated with regard to the reduced NTA production in the process of the present invention. It is considered that a reaction between GN and very strong base produces the NTA. In previously-known processes, approximately four equivalents of GN (i.e., two moles of GN for each —$NH_2$ group on EDA) was mixed with EDA in the presence of caustic. In contrast, in the method of the present invention, in steps (a) and (b), approximately half that amount of GN (i.e., two equivalents, which is one mole of GN for each —$NH_2$ group on EDA) is reacted with EDA. Most or all of that GN will react with EDA to form DN. Because little or no very strong base is present in steps (a) and (b), the two equivalents of GN are used up in step (b) and thus do not produce NTA when DN is converted to DA in the presence of a very strong base. That is, about half the GN used in the overall process of the present invention is consumed at a time when it is not exposed to very strong base. Later in the process of the present invention, in step (d), some GN does come into contact with ammonia in presence of a very strong base, but overall the present invention reduces the amount of GN that comes in contact with very strong base, and that reduction in contact between GN and very strong base is expected to reduce the amount of NTA that is produced.

The following are examples of the present invention. Operations were performed at room temperature, also referred to as ambient temperature (approximately 23° C.), except where otherwise stated.

EXAMPLE 1: PREPARATION OF EDTA

This was a lab-scale demonstration of the inventive process. The 1-L round bottom flask containing a stainless steel frit gas sparger was placed below the liquid level was charged with 37.4 g of ethylenediamine. The reaction was cooled to 5° C., and then 160.0 g of 40 wt % aqueous glycolonitrile was added over 127 minutes, while the solution in the 1-L flask was stirred with overhead stirring at 300 rpm. During the addition, the maximum temperature reached was 12° C. The solution was stirred at 5° C. for one hour, and then at ambient temperature for one hour, which resulted in a light yellow in color solution. The 194.1 g solution (98% mass recovery) was removed from the 1-L flask and placed in an addition funnel. The 1-L flask was rinsed with water, and then charged with 236.1 g of 50 wt % aqueous sodium hydroxide. The caustic solution in the 1-L was warmed to 40° C., and then the Dinitrile solution was added to the 1-L flask from the addition funnel over 145 minutes. An air sparge of 0.6 L/min through the solution using the stainless steel frit to the water scrubbed was used during the addition. The heating mantle was dropped to control the temperature and the addition was paused when the temperature rose above 42° C. The maximum temperature reached was 44° C. The resulting solution was light orange in color. The scrubber pH increased from 4.95 to 5.51 during the addition, and was 5.51 after holding overnight at 40° C. A yellow solid formed overnight, which climbed into the condenser due to the air sparge. The air was shut off. The mixture was warmed to 90° C., which dissolved the yellow solid in the 1-L flask. The temperature was increased to 106° C. with the 0.6 L/min air sparge reestablished in order to provide a reflux and rinse the solid material from the condenser. An additional 26.5 g of water was added. After the solids dissolved and rinsed into the 1-L reactor, the temperature was decreased to 95° C., and then 206.5 g of 40 wt % aqueous glycolonitrile was added over two hours. No significant exotherm was detected based on the temperature profile. The maximum temperature reached during the feed was 95° C. The scrubber pH at the end of the addition was 10.02, and was 9.95 after holding the red reaction solution at 95° C. for three hours. After cooling, the 551.0 g of solution (82.7% mass recovery) were recovered and analyzed.

EXAMPLE 2: PREPARATION OF EDTA

This was a lab-scale demonstration of the process of the present invention. 59.5 g (0.62 mole) of 63 wt % EDA/Water mixture was pre-loaded in a 1 L jacketed reactor. The jacket temperature was set at 20° C. The agitation was set at 300 rpm. 129.3 mL of 40 wt % glycolonitrile solution (1.6 equivalents, 1 mole) was added to EDA at 5 mL/min via an ISCO pump over 26 min. The internal temperature of the reaction mixture rose from 23° C. to 32° C. during the course of addition. The jacket temperature was then set to 40° C., and the reaction mixture was held at temperature for an additional 60 min to ensure complete conversion. The dinitrile reaction mixture at the end of the hold was colorless to pale yellow. A 1 L Hastelloy C Parr reactor was loaded with 224.2 g (2.8 mole) of 50 wt % caustic (NaOH) aqueous solution (4.5 eq.) and 50 mL of deionized (DI) water. The dinitrile (DN) was then fed to the Hastelloy reactor at 2.4 mL/min, while maintaining the reaction solution at room temperature (22° C.). The internal temperature rose from 22° C. to 27° C. during the course of addition. During the DN feed, the agitation was set at 350 rpm and a nitrogen sparge was maintained at 2.5 L/min. The scrubber pH changed from 8.38 to 9.47 during the addition. The reactor mantle temperature was set to 95° C. for an additional 4 hours. 200 mL of DI water was added during the hold to make up for the water loss (336.2 g of water collected in the knock out pot). The scrubber pH changed from 9.47 to 10.0 during this additional hold time. The reaction mixture was held at 85° C. overnight under agitation with no sparge. The reactor contents were heated to 95° C. and nitrogen sparge set to 2.5 L/min prior to the second charge of glycolonitrile. 198 mL (1.53 mole) of 40 wt % glycolonitrile was added to the Parr reactor via an ISCO pump at 2 mL/min over 99 mins. The reaction mixture was held at temperature for an additional 4 hours. The final scrubber pH was 10.4. An additional 280 g of DI water was added during the hold to compensate for the water loss. The reaction mixture was maintained overnight at temperature (85° C.) under air sparge at 1 L/min After cooling, 474.0 g of final product was recovered and analyzed (90% mass accountability).

EXAMPLE 3: PREPARATION OF EDTA

This was a lab-scale demonstration of the inventive process. 59.5 g (0.62 mole) of 63 wt % EDA/Water mixture was loaded in a 1 L jacketed reactor. The jacket temperature was set at 40° C. The agitation was set at 300 rpm. 129.3 mL of 40 wt % glycolonitrile solution (1.6 eq., 1 mole) was added to EDA at 5 mL/min via an ISCO pump over 26 min. The internal temperature of the reaction mixture rose from 35° C. to 39° C. during the course of addition. The reaction mixture was held at temperature for an additional 60 min. to ensure complete conversion. The dinitrile reaction mixture at the end of the hold was colorless to pale yellow. A 1 L Hastelloy C Parr reactor was loaded with 224.2 g (2.8 mole) of 50 wt % caustic aqueous solution (4.5 eq.) and 50 mL of DI water, and then heated to 90° C. The DN solution was then fed to the Hastelloy C reactor at 1.9 mL/min During the entire addition, the agitation was set at 350 rpm and a nitrogen sparge was maintained at 1.0 L/min. The reactor temperature was maintained at 90° C. for an additional 4 hours. 100 mL of DI water was added during the hold to make up for the water loss (110.8 g of water collected in the knock out pot). The reaction mixture was held at 85° C. overnight under agitation with no sparge. The reactor contents were then heated to 90° C. and the nitrogen sparge was set to 2.5 L/min prior to the second charge of glycolonitrile. 198 mL (1.53 mole) of 40% glycolonitrile was added to the Parr reactor via an ISCO pump at 2 mL/min over 99 mins. The reaction mixture was held at temperature for an additional 4 hours. The final scrubber pH was 10.28. An additional 500 g of DI water was added during the hold to compensate for the water loss. The reaction mixture was maintained overnight at temperature under air sparge at 1 L/min. After cooling, 589.0 g of final product was obtained and analyzed (92% mass accountability).

EXAMPLE 4C: COMPARATIVE PREPARATION OF EDTA

This was a lab-scale demonstration of a previously-known process in which very strong base was present from the beginning of the process. 35 g (0.58 mole) of EDA was loaded to a 1 L Hastelloy C Parr reactor. The reactor was then loaded with 209.7 g (2.62 mole) of 50 wt % aqueous caustic solution and 21.0 g of water. The jacket temperature was set to 90° C. The agitation was set at 350 rpm. 305.8 mL of 40 wt % glycolonitrile solution (2.36 mole) was added to the reactor content at 2 mL/min via an ISCO pump over 2.5 hours. The internal temperature of the reaction mixture was maintained at 90° C. during the course of addition. Once ⅓rd of glycolonitrile was added, nitrogen was sparged through the reaction mixture at 1 L/min rate. The reaction mixture was held at temperature for an additional 4 hours to ensure complete conversion, and then overnight at 85° C. without sparging. The final scrubber pH was 10.05. An additional 570 g of DI water was added during the hold to compensate for the water loss. After cooling, 592.6 g of final product was removed from the reactor and analyzed (94% mass accountability).

COMPARATIVE EXAMPLE 5C: COMPARATIVE PREPARATION OF EDTA

This was a lab-scale demonstration of a previously-known process in which very strong base was present from the beginning of the process. A 1-L round bottom flask was outfitted with a glass frit gas sparger placed below the liquid level, a water cooled condenser, an overhead stirrer, an addition funnel, and connected to a water scrubber acidified with acetic acid. After assembly, the 1-L reactor was charged with 113.1 g of 50 wt % sodium hydroxide and 20.14 g of ethylenediamine. The reaction was warmed to 95° C., and then 195 g of 40 wt % aqueous glycolonitrile was added over 79 minutes. The maximum temperature reached was 96° C. An air flow of 2.5 L/min bubbled though the reaction solution was passed through the water scrubber during the reaction. The pH in the scrubber increased from 4.38 to 10.21. Some solids were seen to form on the walls of the 1-L reactor, which were dissolved into the reaction solution by the addition of 60.5 g of water. The solution was stirred at 95° C. to 105° C. for 2.5 hours, and then cooled to unload 316.3 g of reaction solution. Analysis results are shown in Table 1.

EXAMPLE 6C: COMPARATIVE PREPARATION OF EDTA

This was a lab-scale demonstration of a previously-known process in which very strong base was present from the beginning of the process. A 1-L round bottom flask was outfitted with a glass frit gas sparger placed below the liquid level, a water cooled condenser, an overhead stirrer, an addition funnel, and connected to a water scrubber (acidified with acetic acid). The reactor was charged with 133.5 g of 50 wt % sodium hydroxide, 6.8 g of water, and 21.15 g of ethylenediamine, and then the reactor was warmed to 80° C. After reaching 80° C., 206.9 g of 40 wt % aqueous glycolonitrile was added via continuous addition over 91 minutes. The maximum temperature reached was 86° C. An air flow of 2.5 L/min bubbled though the reaction solution was passed through the water scrubber during the feed. The pH in the scrubber increased from 5.42 to 10.28. The solution was stirred at 95° C. overnight, and then cooled to unload 319.4 g of reaction solution.

EXAMPLE 7: PREPARATION OF EDTA

This was a lab-scale demonstration of the inventive process. A 1-L round bottom flask was outfitted with a water cooled condenser, an overhead stirrer, and an addition funnel. The system was placed under a nitrogen atmosphere. The reactor was charged with 97.5 g of 40 wt % aqueous glycolonitrile, and then was cooled to 2° C. Ethylenediamine (22.5 g) was then added dropwise over 55 minutes. During the feed, the maximum temperature reached was 9° C. The addition funnel was rinsed into the 1-L reactor with 16.5 g of water and then fed to the reactor. The solution was warmed to ambient temperature, and then transferred to the addition funnel with 19 g of water. The 1-L flask was charged with 140.7 g of 50 wt % aqueous sodium hydroxide. The nitrogen flow of 2.5 L/min was bubbled though the reaction solution and passed through an acidified (acetic acid) water scrubber. The solution in the 1-L reactor was warmed to 36° C. The solution in the addition funnel was then added to the 1 L reactor over 135 minutes and resulted in a rise in reaction temperature from 36° C. to 44° C. After feeding in the solution from the funnel, water (33 grams) was added to the funnel to rinse down the sides and then added to the 1 L reactor. The pH in the scrubber increased from 4.08 to 9.25. The solution was stirred at 40° C. overnight, and then warmed to 95° C. 128.8 g of 40 wt % aqueous glycolonitrile was then added over about 3 hours. The nitrogen sparge was switched to air for the addition. The scrubber pH increased to 10.48. After holding at 95° C. for an additional 2 hours, the solution was cooled and unloaded to afford 397.2 g of reaction solution.

EXAMPLE 8: PREPARATION OF EDTA

This was a lab-scale demonstration of the inventive process. A 1-L round bottom flask was outfitted with a water cooled condenser, an overhead stirrer, and an addition funnel. The reaction flask was charged with 168.5 g of 40 wt % aqueous glycolonitrile, and then was cooled with an ice bath. The addition funnel was charged with 39.2 g of ethylenediamine. The EDA was then added to the 1 L flask in a manner such that the maximum temperature reached was 12° C. The solution was warmed to 40° C., and then charged with 235.2 g of 50 wt % aqueous sodium hydroxide. An air flow of 2.5 L/min was sparged though the reaction solution and the gas sparged was sent through an acidified (acetic acid) water scrubber to capture ammonia. During the feed, the maximum temperature reached was 48° C. The pH in the scrubber also increased from 4.06 to 9.82 during this time. The solution was stirred at 40° C. overnight, and then warmed to reflux for 1 hour before cooling to 85° C. After reaching 85° C., 214.4 g of 40 wt % aqueous glycolonitrile was added over about 2 hours. After holding at 95° C. overnight, the solution was cooled and unloaded to afford 649.2 g of reaction solution.

EXAMPLE 9: PREPARATION OF EDTA

This was a lab-scale demonstration of the inventive process. 137.4 mL (1.06 mole) of 40 wt % aqueous glycolonitrile solution was loaded to a 1 L jacketed glass reactor. The jacket temperature was set to 0° C. The agitation was set at 300 rpm. 59.5 g (0.62 mole) of 63 wt % EDA/water mixture was added to GN at 1 mL/min via an ISCO pump which took approximately 1 hour. The internal temperature of the reaction mixture rose from 3° C. to 5° C. during the course of addition. The reaction mixture was held at 10° C. for an additional 6 hours to ensure complete conversion. The dinitrile reaction mixture at the end of the hold was colorless to pale yellow. The dinitrile was then transferred to a 1 L jacketed reactor previously loaded with 224.2 g (2.8 mole) of 50 wt % caustic aqueous solution (4.5 eq.) and 60 mL of DI water. The reaction temperature was maintained at 40° C. during the feed (1.9 mL/min). The agitation was set at 350 rpm for the duration of the reaction. An air sparge was maintained at 2.0 L/min during the entire addition. The reactor temperature was maintained at 40° C. for an additional 8-10 hours with air sparge. The reactor contents were distilled between 95° C. to 100° C. for an additional 4 hours with air sparge at 1.0 mL/min prior to the second charge of glycolonitrile. 189.9 mL (1.46 mole) of 40 wt % glycolonitrile was added to the reactor via an ISCO pump at 1 mL/min over 190 mins. The reaction mixture was held at 85° C. for an additional 8 hours under air sparge at 1 L/min. The final scrubber pH was 8.15. An additional 600 g of DI water was added during the hold to compensate for the water loss. After cooling, 577.2 g of final product was analyzed (86% mass accountability).

EXAMPLE 10: TEST RESULTS

The products from Examples 1, 5C, 6C, 7, and 8 were analyzed. The following compounds were detected and reported: EDTA, NTA, SEDDA (symmetrical ethylenediamine-N—N'-diacetic acid=DA), UEDDA (unsymmetrical ethylenediamine-N—N'-diacetic acid), and ED3A (ethylenediaminetriacetic acid). The results were as follows. The amounts shown are weight percent, based on the total weight of the final products.

| Example | Comment | SEDDA | UEDDA | ED3A | EDTA | NTA |
|---|---|---|---|---|---|---|
| 1 |  | 0.718 | 0 | 0.90 | 21.27 | 3.25 |
| 5C | comparative | 0.67 | 0 | 2.71 | 22.9 | 3.49 |
| 6C | comparative | 1.08 | 0.19 | 1.77 | 20.0 | 4.65 |
| 7 | add DN to base | 1.03 | 0 | 0.63 | 21.8 | 2.22 |
| 8 | add base to DN | 1.11 | 0 | 0.49 | 22.9 | 2.13 |

All of the examples showed comparably good productivity for making EDTA, and the inventive examples had lower NTA than the comparative examples.

It is considered that the above laboratory-scale examples demonstrate that a change from the comparative method of making EDTA to the inventive method of making EDTA results in comparable yield of EDTA and reduced production of NTA. It is considered that these results indicate that significant reduction of NTA production would be obtained if the same comparison were made at a larger scale (e.g., production scale). That is, it is considered that the NTA produced in a large-scale operation of the method of the present invention would be less than the NTA produced in a large-scale operation of the comparative method.

The invention claimed is:

1. A method of making ethylenediaminetetraacetic acid (EDTA) comprising the steps:
   (a) providing a reaction mixture (a) comprising ethylenediamine (EDA) and glycolonitrile (GN), wherein reaction mixture (a) comprises 0% to 0.1% by weight, based on the weight of reaction mixture (a), of any base having pKa of the conjugate acid (PKaH) of 13 or higher;
   (b) causing or allowing reaction mixture (a) to react to form a dinitrile compound having structure DN:

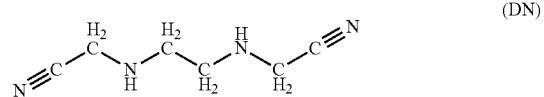

(DN)

(c) bringing the DN into contact with aqueous solution of a base having pKaH of 11 or higher, and causing or allowing the resulting mixture to react to form a diacid compound having structure DA:

(DA)

wherein each —R has the following structure:

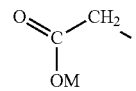

wherein each M is independently hydrogen or an alkali metal;
   (d) causing or allowing the DA to react, either sequentially or simultaneously, with additional GN to form products (Pd);
   (e) causing or allowing products (Pd) to react with a base having pKaH of 11 or higher to form EDTA.

2. The method of claim 1, wherein reaction mixture (a) is formed by placing all the EDA used in step (a) into a vessel, optionally in the form of an aqueous solution, wherein the amount of GN in the vessel, by weight based on the weight of EDA in the vessel, is 0 to 0.1%, and then adding GN, optionally in the form of an aqueous solution, to the vessel.

3. The method of claim 1, wherein reaction mixture (a) is formed by bringing an aqueous solution of EDA into contact with an aqueous solution of GN.

4. The method of claim 1, wherein step (b) is conducted at a temperature of 0° C. to 10° C.

5. The method of claim 1, wherein, in reaction mixture (a), the mole ratio of GN to EDA is 3:1 or lower.

6. The method of claim 1, wherein, at the conclusion of step (e), the weight ratio of EDTA to nitrilotriacetic acid is 7:1 or higher.

* * * * *